(12) United States Patent
Oonishi (10) Patent No.: US 10,493,216 B2
(45) Date of Patent: Dec. 3, 2019

(54) METHOD FOR PRODUCING A NEEDLE-EQUIPPED SYRINGE (71) Applicant: TERUMO KABUSHIKI KAISHA, Tokyo (JP)

(72) Inventor: Shuuichi Oonishi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 354 days.

(21) Appl. No.: 15/280,568

(22) Filed: Sep. 29, 2016

(65) Prior Publication Data

US 2017/0014580 A1 Jan. 19, 2017

Related U.S. Application Data (63) Continuation of application No. PCT/JP2015/058948, filed on Mar. 24, 2015.

(30) Foreign Application Priority Data

Mar. 31, 2014 (JP) .................................. 2014-071911

(51) Int. Cl.
B29C 45/14 (2006.01)
A61M 5/34 (2006.01)
(Continued)

(52) U.S. Cl.
CPC ............ *A61M 5/34* (2013.01); *A61M 5/3129* (2013.01); *B29C 45/14065* (2013.01);
(Continued)

(58) Field of Classification Search
None
See application file for complete search history.

(56) References Cited

U.S. PATENT DOCUMENTS 3,330,004 A * 7/1967 Cloyd ................... A61M 5/343
249/97
5,510,065 A * 4/1996 McFarlane ........ B29C 45/14598
264/313
(Continued)

FOREIGN PATENT DOCUMENTS

JP H09-066104 A 3/1997
JP 2011-510836 A 4/2011
(Continued)

OTHER PUBLICATIONS

International Search Report issued in International Patent Application No. PCT/JP2015/058948 dated Jun. 23, 2015.

*Primary Examiner* — Edmund H Lee
(74) *Attorney, Agent, or Firm* — Foley & Lardner LLP (57) ABSTRACT An injection molding die for molding a needle-equipped syringe includes a male die including a core pin, and a through hole, a female die including a female die opening part, a concave part, and an injection needle holding hole; a support rod that is insertable from a pin proximal end into the through hole, wherein the support rod is configured to contact and support a needle proximal end of an injection needle inserted from a pin distal end, and to push the needle proximal end to a vicinity of the pin distal end; and a resin injection gate configured to allow resin to be injected to a cavity formed by the concave part and the core pin inserted from the female die opening part.

6 Claims, 7 Drawing Sheets (51) Int. Cl.
*A61M 5/31* (2006.01)
*B29L 31/00* (2006.01)
*A61M 5/28* (2006.01)
*B29C 45/00* (2006.01)

(52) U.S. Cl.
CPC ............... *A61M 5/28* (2013.01); *A61M 5/343* (2013.01); *A61M 2207/00* (2013.01); *B29C 45/14418* (2013.01); *B29C 45/14426* (2013.01); *B29C 45/14598* (2013.01); *B29C 2045/0027* (2013.01); *B29C 2045/14139* (2013.01); *B29L 2031/7544* (2013.01)

(56) References Cited

U.S. PATENT DOCUMENTS

| | | | | |
|---|---|---|---|---|
| 5,830,401 A | * | 11/1998 | Prichard | A61M 25/0014 264/262 |
| 7,842,217 B2 | * | 11/2010 | Enns | A61J 15/00 264/241 |
| 8,496,862 B2 | * | 7/2013 | Zelkovich | A61M 5/343 264/259 |
| 8,790,312 B2 | * | 7/2014 | Togashi | A61M 5/346 604/187 |
| 9,724,859 B2 | * | 8/2017 | Zahn | A61M 5/343 |
| 2010/0145284 A1 | * | 6/2010 | Togashi | A61M 5/346 604/218 |
| 2010/0270702 A1 | * | 10/2010 | Zelkovich | A61M 5/343 264/278 |
| 2011/0254202 A1 | * | 10/2011 | Aeschlimann | A61M 5/158 264/328.1 |
| 2012/0010573 A1 | * | 1/2012 | Lundquist | A61M 5/3293 604/192 |
| 2013/0138047 A1 | * | 5/2013 | Takemoto | A61M 5/343 604/192 |
| 2014/0070453 A1 | * | 3/2014 | Dietl | A61M 5/34 264/275 |

FOREIGN PATENT DOCUMENTS

| | | |
|---|---|---|
| JP | 2013-070892 A | 4/2013 |
| WO | WO-2008/139982 A1 | 11/2008 |
| WO | WO-2009/091895 A2 | 7/2009 |

* cited by examiner

METHOD FOR PRODUCING A NEEDLE-EQUIPPED SYRINGE

CROSS-REFERENCE TO RELATED APPLICATIONS

The present application is a bypass continuation of PCT Application No. PCT/JP2015/058948, filed on Mar. 24, 2015, which claims priority to Japanese Application. No. 2014-071911, filed on Mar. 31, 2014. These applications are hereby incorporated by reference in their entireties.

BACKGROUND

The present disclosure relates to an injection molding die used to mold a needle-equipped syringe used to inject a small amount of drug solution under the skin, and a method for producing the needle-equipped syringe using the injection molding die.

The needle-equipped syringe is a syringe in which a thin injection needle penetrates the distal end of a barrel to be used as the syringe barrel and is fixed to the barrel. A gasket is attached to the distal end of a plunger and the plunger is inserted in the barrel. This enables the needle-equipped syringe to rapidly discharge a small amount of drug solution in the barrel from the injection needle by strongly pressing the drug solution with the plunger. Thus, the needle-equipped syringe is used for hypodermic injection rather than intravenous injection. The needle-equipped syringe includes the barrel to which the injection needle is fixed. Accordingly, the needle-equipped syringe does not require a complicated operation for attaching a separate injection needle hub immediately before the administration, and allows for easy and efficient administration of the drug solution. Thus, the needle-equipped syringe is used for general purposes.

The needle-equipped syringe is produced with a manner in which a barrel including an insertion hole opening on the distal end of the barrel is produced, and an injection needle is inserted into and adhered to the insertion hole with adhesive. For pain relief during administration, a low dosage—for example, about 500 µL of a biological product such as a vaccine is administrated by hypodermic injection. The injection needle adhered to the needle-equipped syringe has a small diameter. This often raises the pressure on the plunger too high when a small amount of drug solution is administrated. This may cause the injection needle to disconnect from the distal end of the barrel.

In light of the foregoing, a needle-equipped syringe to which an injection needle is more strongly fixed (rather than adhered) has been developed. For example, as described in JP 2013-70892 A, a needle-equipped syringe in which a barrel and an injection needle provided on the distal end of the barrel are integrally formed is produced by injection molding in which resin is injected into an injection molding die on which the injection needle is provided. The needle-equipped syringe produced as describe above includes the injection needle directly and firmly fixed to the nozzle part of the barrel. Accordingly, the injection needle does not disconnect from the distal end of the barrel even when a high pressure is applied. Thus, the needle-equipped syringe is extremely safe.

Figure 6:
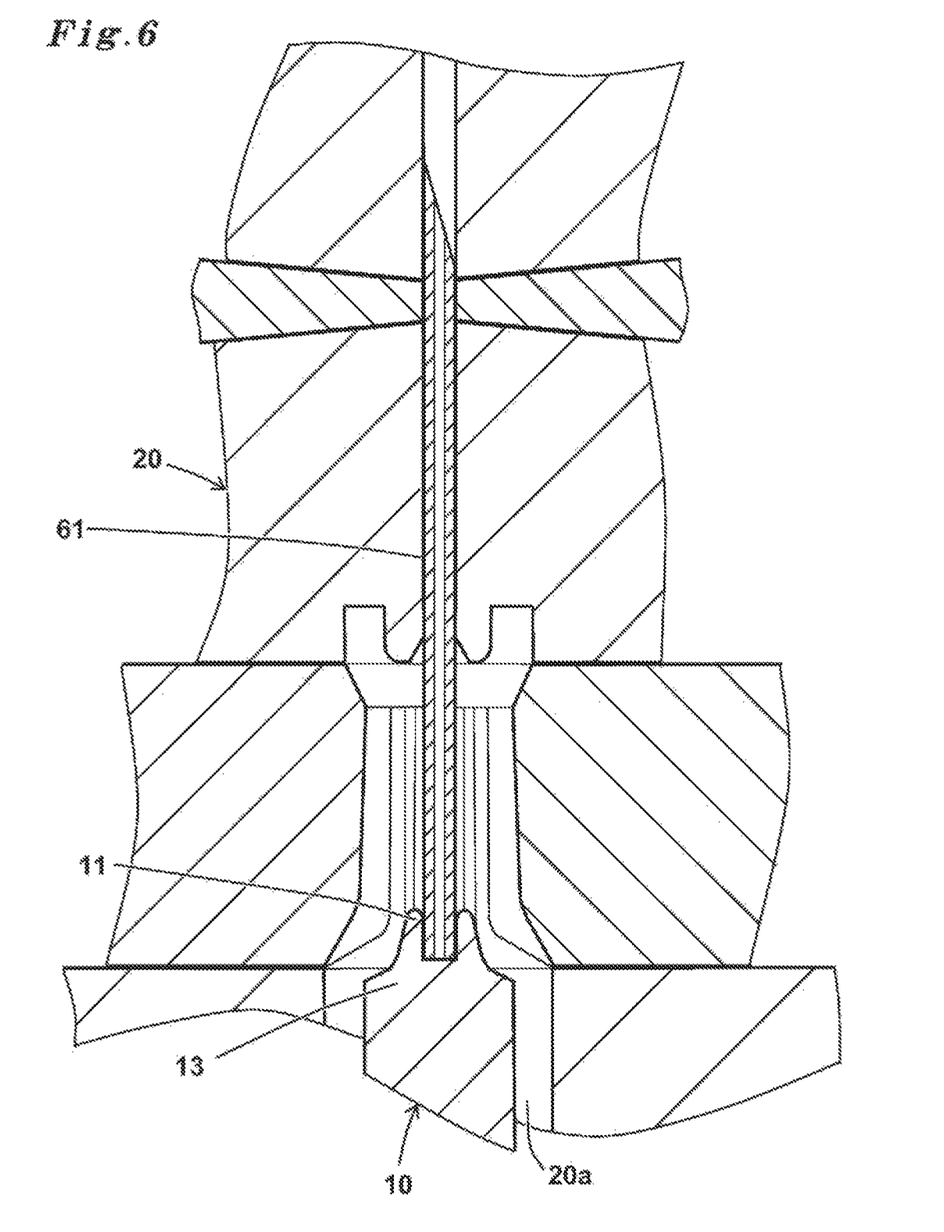
FIG. 6 is an enlarged partial cross-sectional front view of the main parts of an injection molding die that is known in the art.

A conventional injection molding die used to produce the needle-equipped syringe in injection molding, illustrated in FIG. 6, includes: a male die 10 provided with a protrusion 11 that supports the injection needle 61 so that the injection needle 61 is deeply inserted in the distal end of the core pin 13 and stands independently; and a female die 20 that forms the external surface of the barrel. A shallow insertion of the injection needle 61 into the protrusion 11 may cause an inclination of the injection needle 61 in the middle of the formation of the cavity 20a. This may causes the inclination of the central axis of the injection needle 61 of the needle-equipped syringe molded by the injection of resin after the formation with respect to the central axis of the barrel. In light of the foregoing, the protrusion 11 has a height and a thickness to some degree so that the injection needle 61 can deeply be inserted in the protrusion 11. As a result, the protrusion 11 is transferred such that a deep and wide recessed part is formed on the inner wall of the distal end of the molded barrel. The injection needle is fixed so that the proximal end of the needle is embedded in the recessed part. The recessed part is left as a "dead space." The drug solution with which the recessed part is filled can reach no less than tens to a hundred and several tens µL. When the plunger presses the gasket, the distal end of the gasket comes into contact with the inner wall of the distal end of the barrel. This stops the plunger from pressing the gasket any more. Thus, the drug solution with which the recessed part is filled is not push out. The drug solution remains in the recessed part without discharge, and is wasted.

In light of the foregoing, in order to efficiently use a limited batch of drug solution such as seasonal flu vaccine, there is a need for producing needle-equipped syringes with a minimum dead space so that as many needle-equipped syringes as possible can be produced.

SUMMARY

To solve the problem described above, one objective of certain embodiments of the present invention is to provide an injection molding die that can fix the injection needle to the barrel without inclining the injection needle and can produce a needle-equipped syringe with a minimum dead space hindering the discharge of the filled drug solution; a method for easily producing as many needle-equipped syringes as possible at a high yield using the injection molding die; and a needle-equipped syringe that is produced by the method and that enables nearly complete discharge of the filled drug solution.

An injection molding die according to one embodiment is configured to mold a needle-equipped syringe including a barrel and an injection needle, the barrel including a cylindrical body, a nozzle part provided on a distal end of the body, and an opening part provided on a proximal end of the body, the barrel being made of resin, the injection needle including a needle distal end and a needle proximal end, the needle proximal end being held by the nozzle part, the injection needle and the barrel being integrally formed, the injection molding die comprising: a male die including a core pin and a through hole, the core pin including a pin distal end and a pin proximal end, the core pin configured to form an internal surface of the barrel, the through hole penetrating the core pin from the pin distal end to the pin proximal end and configured that the needle base end of the injection needle is inserted from the pin distal end into the through hole; a female die including a female die opening part, a concave part, and an injection needle holding hole, the concave part communicating with the female die opening part, the concave part configured to form an external surface of the barrel, the injection needle holding hole being provided on a side opposite to the female die opening part and coaxially with the through hole, the injection needle holding hole communicating with the concave part, the injection needle holding hole configured to hold the injection needle; a support rod inserted from the pin proximal end into the through hole, the support rod configured to contact and support the needle proximal end of the injection needle inserted from the pin distal end, the support rod configured to push up the needle proximal end to a vicinity of the pin distal end; and a resin injection gate configured to be that the resin is injected from the resin injection gate to a cavity formed of the concave part and the core pin inserted from the female die opening part.

In the injection molding die, it is preferable that a gradual push-up of the support rod is configured to be adjusted so that the distance between a distal end of the support rod pushed up and the pin distal end is 1.5 mm or less.

In the injection molding die, it is preferable that the core pin includes a protrusion on the pin distal end, the protrusion configured to prevent the resin from entering the injection needle by surrounding the needle proximal end.

In the injection molding die, it is preferable that an outer diameter of the protrusion is 1.5 mm or less, and a height of the protrusion is 1.5 mm or less.

In the injection molding die, it is preferable that the male die includes a cooling mechanism in the core pin, and the cooling mechanism is configured to cool the resin inserted from the resin injection gate by thermal conduction.

In the injection molding die, it is preferable that the female die includes clamping units configured to clamp the injection needle in the injection needle holding hole.

A method for producing a needle-equipped syringe using an injection molding die, the needle-equipped syringe including a barrel and an injection needle, the barrel including a cylindrical body, a nozzle part provided on a distal end of the body, and an opening part provided on a proximal end of the body, the barrel being made of resin, the injection needle including a needle distal end and a needle proximal end, the needle proximal end being held by the nozzle part, the method comprising: preparing a male die, a female die, and a support rod, the male die including a core pin and a through hole, the core pin including a pin distal end and a pin proximal end, the core pin configured to form an internal surface of the barrel, the through hole penetrating the core pin from the pin distal end to the pin proximal end, the female die including a female die opening part, a concave part, and an injection needle holding hole, the concave part communicating with the female die opening part, the concave part configured to form an external surface of the barrel, the injection needle holding hole being provided on a side opposite to the female die opening part and coaxially with the through hole, the injection needle holding hole communicating with the concave part, the support rod inserted from the pin proximal end into the through hole; inserting the injection needle from the needle proximal end into the through hole from the pin distal end, and poking and supporting the needle proximal end of the injection needle by the support rod; forming a cavity formed of the concave part and the core pin by inserting the core pin from the female die opening part into an internal hollow of the concave part; pushing up the needle proximal end to a vicinity of the pin distal end by gradually pushing up the support rod inserted in the through hole, and holding the injection needle in the injection needle holding hole; and integrally forming the injection needle and the barrel by injecting the resin in the cavity.

In the method for producing a needle-equipped syringe, it is preferable that gradually pushing up the support rod until the distance between the distal end of the support rod and the pin distal end is 1.5 mm or less.

In the method for producing a needle-equipped syringe, it is preferable that a protrusion configured to prevent the resin from entering the through hole by surrounding the needle proximal end is formed on the pin distal end, and wherein forming a recessed part corresponding to the protrusion in the barrel by injecting the resin into the cavity and embedding the needle proximal end in the recessed part.

In the method for producing a needle-equipped syringe, it is preferable that the protrusion is formed so that an outer diameter of the protrusion is 1.5 mm or less, and a height of the protrusion is 1.5 mm or less.

In the method for producing a needle-equipped syringe, it is preferable that clamping units configured to clamp the injection needle in the injection needle holding hole are provided in the female die, and wherein supporting the injection needle pushed up by a gradual push-up of the support rod in the injection needle holding hole and clamping the injection needle by the clamping units.

In the method for producing a needle-equipped syringe, it is preferable that a cooling mechanism configured to cool the resin injected from the resin injection gate by thermal conduction is provided in the core pin, and wherein cooling and solidifying the resin inserted in the cavity with the cooling mechanism so that the injection needle and the barrel are integrally formed, and removing the integrally-formed injection needle and barrel.

A needle-equipped syringe according to one embodiment includes: a barrel including a cylindrical body, a nozzle part provided on a distal end of the body, and an opening part provided on a proximal end of the body, the barrel being made of resin; and an injection needle held by the nozzle part, wherein the injection needle and the barrel are integrally formed, and the body is configured to be able to be filled with drug solution, wherein a recessed part is formed on the proximal end of the nozzle part, the recessed part surrounded by an inner wall of the barrel and recessed toward distally, wherein an outer diameter of the recessed part is 1.5 mm or less, and a height of the recessed part is 1.5 mm or less, and wherein a needle proximal end of the injection needle protrudes in the recessed part by 1.5 mm or less.

The injection molding die according to certain embodiments of the present invention is configured to mold a needle-equipped syringe in a manner in which a through hole penetrates a core pin from the pin distal end to the pin proximal end of the core pin, a support rod is inserted from the pin proximal end in the through hole, and the support rod supports the injection needle inserted from the pin distal end and pushes up the injection needle when resin is injected. Using the injection molding die allows the injection needle to deeply be inserted into the through hole and be supported by the support rod when the male die and the female die form a cavity, and thus prevents the injection needle from inclination. Thus, the injection needle can be fixed to the barrel without inclination. This can form a needle-equipped syringe with a small dead space.

According to the method for producing a needle-equipped syringe of the present certain embodiments of the present invention, the injection needle is deeply inserted into the through hole of the injection molding die, and the support rod pushes up the injection needle as high as possible while supporting the injection needle in order to prevent the injection needle from inclination. This can efficiently and easily mold a needle-equipped syringe with a small dead space at a high yield.

In the needle-equipped syringe according to certain embodiments of the present invention, the needle proximal end of the injection needle hardly protrudes in the internal hollow of the barrel, and thus the recessed part of the inner wall of the nozzle part surrounding the protrusion is extremely small. This reduces the dead space. The reduced dead space allows for nearly complete discharge of the filled drug solution. Additionally, the rate of defective products in which the central axis of the injection needle and the central axis of the body of the barrel are misaligned is low among the needle-equipped syringes. The needle-equipped syringes can be produced at a high yield. The needle-equipped syringes are highly safe and reliable.

DETAILED DESCRIPTION

Hereinafter, embodiments of the present invention will be described in detail. However, the scope of the present invention is not limited to the embodiments described below.

Figure 1:
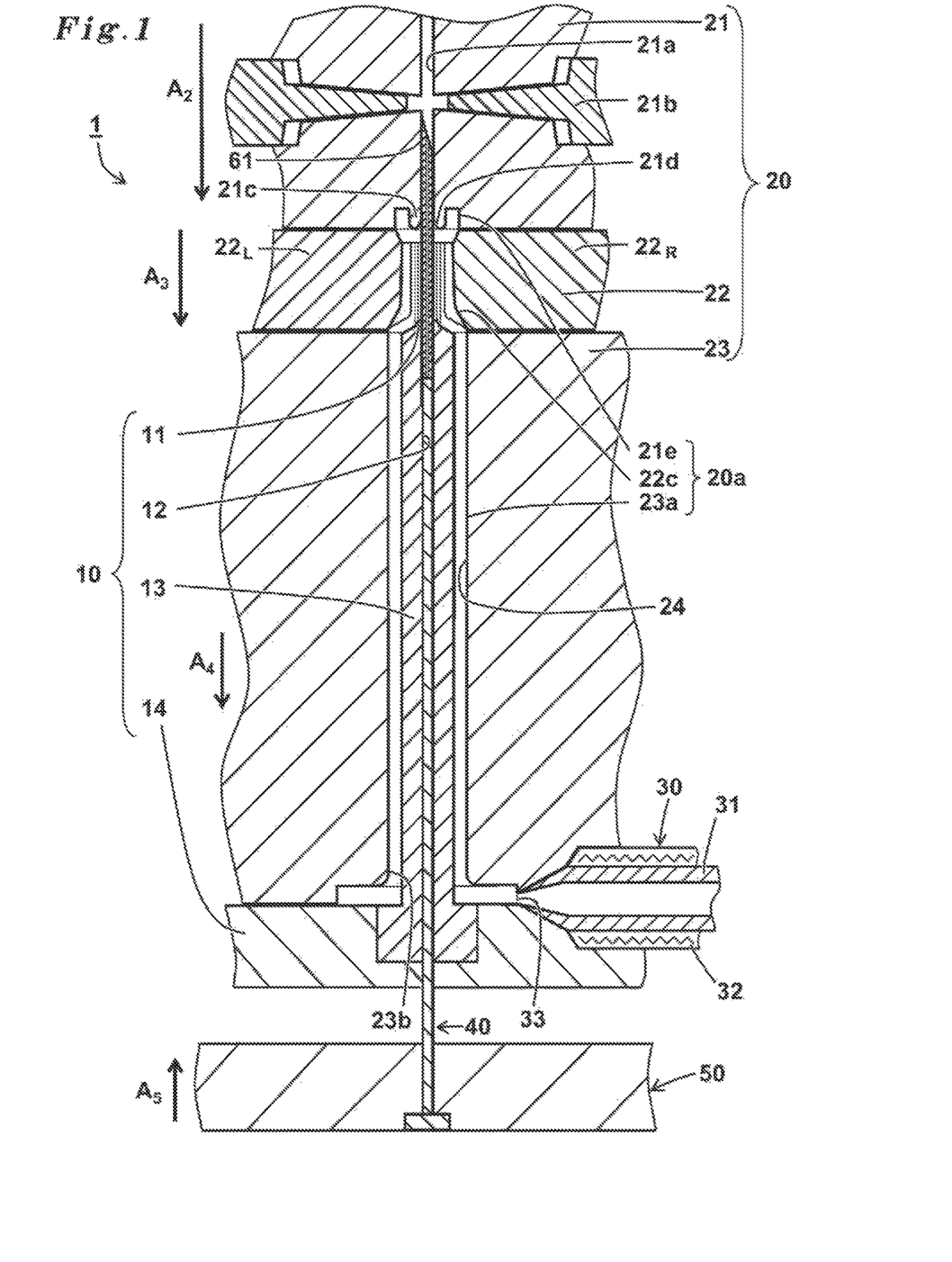
FIG. 1 is a schematic cross-sectional front view of a state before an injection needle is pushed up while an injection molding die of the present invention is used.

FIG. 1 is a schematic cross-sectional front view of an embodiment of an injection molding die 1 of the present invention. The injection molding die 1 is configured to mold a needle-equipped syringe 60 including an injection needle 61 and a barrel 62 to which the injection needle 61 is fixed (see FIG. 4A). The injection molding die 1 includes: a male die 10 including a core pin 13 that forms an internal surface of the barrel 62 of the needle-equipped syringe 60, a fixing plate 14 to which the pin proximal end of the core pin 13 is fitted, and a through hole 12 into which the injection needle 61 that is a metal cylindrical needle is inserted from the pin distal end of the core pin 13; a support rod 40 inserted from the pin proximal end of the core pin 13 into the through hole 12; a female die 20 including a concave part 24 that forms the external surface of the barrel 62 and communicates with the female die opening part 23b; and a resin injection gate 33 used to inject resin into the cavity 20a formed of the male die 10 and the female die 20. The support rod 40 has contact with the needle proximal end of the injection needle 61 inserted in the through hole 12 and can push up the injection needle 61. FIG. 1 illustrates a state before the support rod 40 pushes up the injection needle 61.

The core pin 13 of the male die 10 has a columnar shape and an even diameter between the pin distal end and pin proximal end of the core pin 13. The pin distal end is formed in a substantially conical shape. The top of the pin distal end includes a protrusion 11. The proximal end part of the core pin 13 has a cylindrical column shape with an expanded diameter. The incline of the substantially conical shape is steeper at the protrusion 11 than at the base of the substantially conical shape near the distal end of the core pin 13. The through hole 12 penetrates the central axis of the core pin 13 from the pin distal end to pin proximal end. The inner diameter of the through hole 12 is slightly larger than the outer diameter of the injection needle 61 so that there is some play making it easy to insert the injection needle 61.

The outer diameter of the protrusion 11 is equal to or smaller than 1.5 mm, and is preferably equal to or smaller than 1.0 mm, and more preferably equal to or smaller than 0.5 mm. The height of the protrusion 11 is equal to or lower than 1.5 mm, and is preferably equal to or lower than 1.0 mm, and more preferably equal to or lower than 0.5 mm. Note that the smaller protrusion 11 is more preferable. The protrusion 11 is not necessarily required.

The through hole 12 is formed in a cylindrical shape and has the inner diameter slightly larger than the outer diameter of the injection needle 61. The difference between the inner diameter of the through hole 12 and the outer diameter of the injection needle 61 provides slight play large enough to insert and push up the injection needle 61. This play prevents the through hole 12 from scratching the surface of the inserted injection needle 61 and prevents the injection needle 61 from inclination.

The fixing plate 14 includes a fitting hole into which the pin proximal end of the core pin 13 having a columnar shape and the expanded diameter is fitted. The core pin 13 is fitted into the fitting hole and vertically supported. The through hole 12 penetrates the fixing plate 14 while coaxially extending from the fitting hole to bottom surface of the fixing plate 14 in the same diameter.

The support rod 40 is inserted into the through hole 12 from the pin proximal end of the core pin 13 through the fixing plate 14. The distal end of the support rod 40 has contact with the injection needle 61. This contact causes the support rod 40 to support the injection needle 61 by poking and pushing up the injection needle 61. This prevents the injection needle 61 from dropping from the through hole 12. A distal end surface of the support rod 40 has a concave surface of which center is recessed so as to support the injection needle 61 in the minimum contact with the proximal end of the injection needle 61.

The proximal end of the support rod 40 is stuck and fixed to the drive plate 50 that gradually pushes up the support rod 40. The drive plate 50 is connected to an up-and-down drive source (not illustrated). This connection enables the distal end surface of the support rod 40 to move up and down in the through hole 12 and adjust the vertical position of the injection needle 61 inserted in the through hole 12.

The female die 20 includes: a body forming female die 23 mounted on the fixing plate 14 and configured to mold a body 65 and a flange 68 of the barrel 62; a nozzle part forming female die 22 mounted on the body forming female die 23 and configured to mold the proximal end of the nozzle part 63 of the barrel 62; and a needle holding female die 21 mounted on the nozzle part forming female die 22 and configured to mold a head 63a of the nozzle part 63 (see FIG. 4B) and hold the injection needle 61 when the barrel 62 is molded.

The body forming female die 23 includes: a body forming space 23a configured to form a cavity 20a corresponding to the body 65 and the flange 68 of the barrel 62 (see FIG. 4A) between the body forming female die 23 and the core pin 13 penetrating the body forming female die 23; and a female die opening part 23b from which the core pin 13 is inserted into the body forming space 23a. The female die opening part 23b and the body forming space 23a are arranged coaxially with the core pin 13.

The nozzle part forming female die 22 is provided with a nozzle forming space 22c on the surface of the nozzle part forming female die 22 facing the body forming female die 23. The nozzle forming space 22c is a recessed part used to form a pleated skirt 63c of the nozzle part 63 of the barrel 62 (see FIG. 4B). The nozzle forming space 22c is placed coaxially with the core pin 13.

Figure 4A:
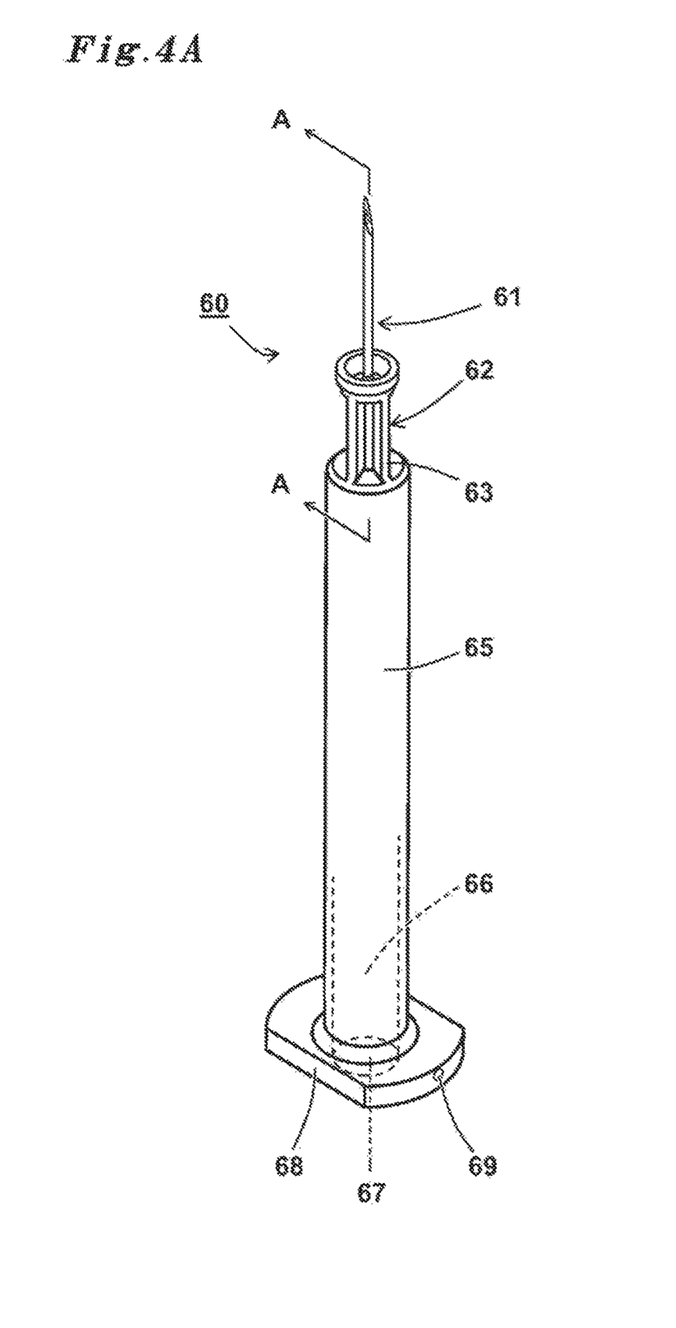
FIG. 4A is a perspective view of a needle-equipped syringe according to one embodiment of the present invention.
Figure 4B:
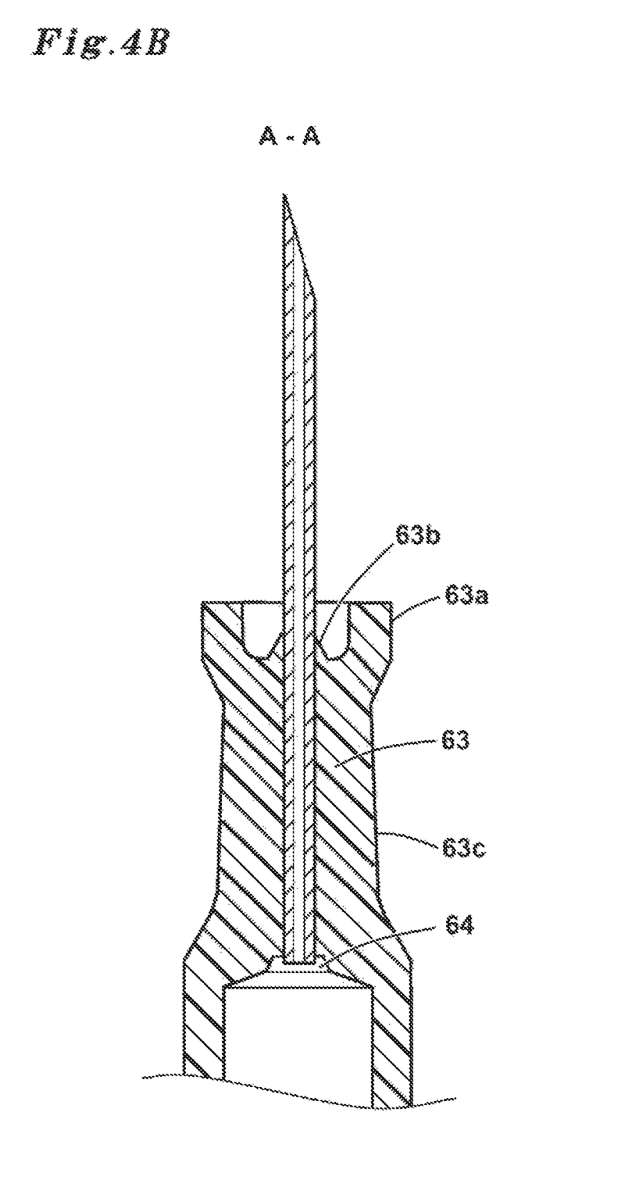
FIG. 4B is an enlarged cross-sectional view of a part of the needle-equipped syringe according to one embodiment of the present invention.

Note that the nozzle part forming female die 22 includes a left die $22_L$ and a right die $22_R$ that can be separate into right and left in order to remove the head 63a and pleated skirt 63c of the nozzle part 63 formed in the head forming space 21e (see FIG. 4B). Symmetrically putting the left die $22_L$ and right die $22_R$ together and merging the separate surfaces form the nozzle forming space 22c.

The needle holding female die 21 includes on the surface facing the nozzle part forming female die 22 a head forming space 21e and an injection needle holding hole 21a. The head forming space 21e is used to form the head 63a of the nozzle part 63. The injection needle holding hole 21a holds the injection needle 61. The injection needle holding hole 21a and the through hole 12 are coaxially arranged.

The peripheral edge of the head forming space 21e is larger than the nozzle forming space 22c. The center of the head forming space 21e is provided with a convex part 21c surrounding the opening part of the injection needle holding hole. A part of the convex part 21c that is an edge of the opening part of the injection needle holding hole is chamfered so that an inclined part 21d that slightly extends the opening part of the injection needle holding hole is formed. This smoothly introduces and inserts the injection needle 61 into the injection needle holding hole 21a even when the injection needle 61 is slightly inclined.

The surface of the convex part 21c and the internal surface of the head forming space 21e are preferably pear-skin finished or roughened in order to facilitate the removal of the resin from the parts.

Furthermore, the needle holding female die 21 is provided with a pair of clamping units 21b configured to clamp the injection needle 61. The pair of clamping units 21b detachably penetrates the needle holding female die 21 in a direction perpendicular to the direction of the axis of the injection needle 61 so that the pair of clamping units 21b can clamp and fix the pushed-up injection needle 61 while the central axis of the injection needle 61 and the central axis of the core pin 13 are substantially aligned in the injection needle holding hole 21a.

The nozzle part forming female die 22 is mounted on the body forming female die 23. Additionally, the needle holding female die 21 is mounted on the nozzle part forming female die 22. This forms the concave part 24 including the body forming space 23a, the nozzle forming space 22c, and the head forming space 21e. The concave part 24 corresponds to the external shape of the barrel 62 in order to form the external surface of the barrel 62.

The core pin 13 is coaxially inserted into the concave part 24. The concave part 24, the core pin 13, and the fixing plate 14 form the cavity 20a used to mold the barrel 62 when the body forming female die 23 has contact with the fixing plate 14. The core pin 13, the nozzle forming space 22c, and the injection needle holding hole 21a are coaxially arranged in the cavity 20a. The cavity 20a forms a space large enough to form the body 65 and nozzle part 63 of the barrel 62 and the flange 68 of the needle-equipped syringe 60 in predetermined thicknesses.

The resin injection gate 33 is used to inject resin into the cavity 20a. The resin injection gate 33 is provided only on a side of the body forming female die 23 so as to form the side surface of an end of the flange 68. A resin injection nozzle 30 used to introduce and inject the thermally-melt thermoplastic resin into the cavity 20a is connected to the resin injection gate 33. The resin injection nozzle 30 includes a tubular runner 31 through which the thermally-melt thermoplastic resin flows. The runner 31 communicates with the cavity 20a forming the flange 68 so as to fill the cavity 20a with the resin through the resin injection gate 33. A heater 32 that maintains a state in which the resin in the runner 31 is melt is provided around the runner 31.

The female die 20 is coupled to an up-and-down drive source (not illustrated) that causes the dies 21, 22, and 23 to cooperate with each other or is coupled to a plurality of up-and-down drive sources (not illustrated) that cause the dies 21, 22, and 23 to separately operate, respectively, so that the body forming female die 23 comes into contact with the fixing plate 14, the nozzle part forming female die 22 comes into contact with the body forming female die 23, and the needle holding female die 21 comes into contact with the nozzle part forming female die 22 sequentially. The contacts form the female die 20 for injection molding. Finally, the drive plate 50 can be coupled to an up-and-down drive source (not illustrated) that causes the drive plate 50 to cooperate with the dies 21, 22, and 23 or to operate separately from the dies 21, 22, and 23 so that the drive plate 50 has contact with the fixing plate 14. The female die 20 is coupled to the up-and-down drive source (s) so that the dies of the female die 20 are divided in reverse order in order to remove the needle-equipped syringe 60 from the female die 20 after the injection molding.

The distal end of the core pin 13 can substantially be formed in a hemispherical shape or a halved polyhedral shape. The external shape of the protrusion 11 can substantially be formed in a frustum of a cone, a hemispherical shape, or a frustum of a pyramid.

The needle holding female die 21 and/or the body forming female die 23 can be a pair of dies that face each other and can open and close in a direction perpendicular to the direction of the axis of the core pin 13.

An example in which the needle holding female die 21, the nozzle part forming female die 22, the body forming female die 23, and the drive plate 50 are driven based on the immovable fixing plate 14 has been described. Anyone of the needle holding female die 21, the nozzle part forming female die 22, the body forming female die 23, the drive plate 50, and the fixing plate 14 may be immovable or all of them may be movable as long as the needle holding female die 21, the nozzle part forming female die 22, the body forming female die 23, the drive plate 50, and the fixing plate 14 relatively operate similarly to the example.

The injection molding die 1 is used to produce a needle-equipped syringe 60 as described below.

First, the needle holding female die 21, the nozzle part forming female die 22, the body forming female die 23, the fixing plate 14, and the drive plate 50 are separate from each other. Meanwhile, the core pin 13 of the male die 10 is completely removed from the body forming space 23a of the body forming female die 23. Additionally, the support rod 40 is inserted in the through hole 12 of the core pin 13. The nozzle part forming female die 22 is formed of the left die $22_L$ and right die $22_R$ put together.

First, the support rod 40 is gradually pushed up so that the injection needle 61 is inserted into the through hole 12 deeply enough to cause the tip of the injection needle 61 to protrude from the through hole 12. The needle proximal end of the injection needle 61 is inserted into the through hole 12, and the support rod 40 contacts and supports the injection needle 61. The body forming female die 23 is placed at a position higher than the needle distal end of the injection needle 61 so that the body forming space 23a and the core pin 13 are coaxially arranged. While the central axis of the core pin 13 and the central axis of female die opening part 20 are aligned, the body forming female die 23 moves in a closing direction $A_4$ until the body forming female die 23 comes into contact with the fixing plate 14. This movement inserts the core pin 13 into the body forming space 23a.

Next, the nozzle part forming female die 22 is placed at a position higher than the needle distal end of the injection needle 61 so that the nozzle forming space 22c and the core pin 13 are coaxially arranged. While the central axes of the nozzle forming space 22c and the core pin 13 are aligned, the nozzle part forming female die 22 moves in a closing direction $A_3$ until the nozzle part forming female die 22 comes into contact with the body forming female die 23.

Furthermore, the needle holding female die 21 is placed at a position higher than the needle distal end of the injection needle 61 so that the injection needle holding hole 21a and the core pin 13 are coaxially arranged. While the central axes of the injection needle holding hole 21a and the core pin 13 are aligned, the injection needle 61 is inserted into the injection needle holding hole 21a and the needle holding female die 21 moves in a closing direction $A_2$ until the needle holding female die 21 comes into contact with the nozzle part forming female die 22. The movement inserts the tip part of the injection needle 61 into the injection needle holding hole 21a. Meanwhile, the tip of the injection needle 61 is placed at a position lower than the clamping units 21b.

Then, the concave part 24 including the body forming space 23a, the nozzle forming space 22c, and the head forming space 21e is formed in the female die 20. The cavity 20a is formed between the female die 20 and the male die 10. The injection needle 61 is deeply inserted in the core pin 13. This deep insertion prevents the injection needle 61 from being inclined when the cavity 20a is formed.

Figure 2:
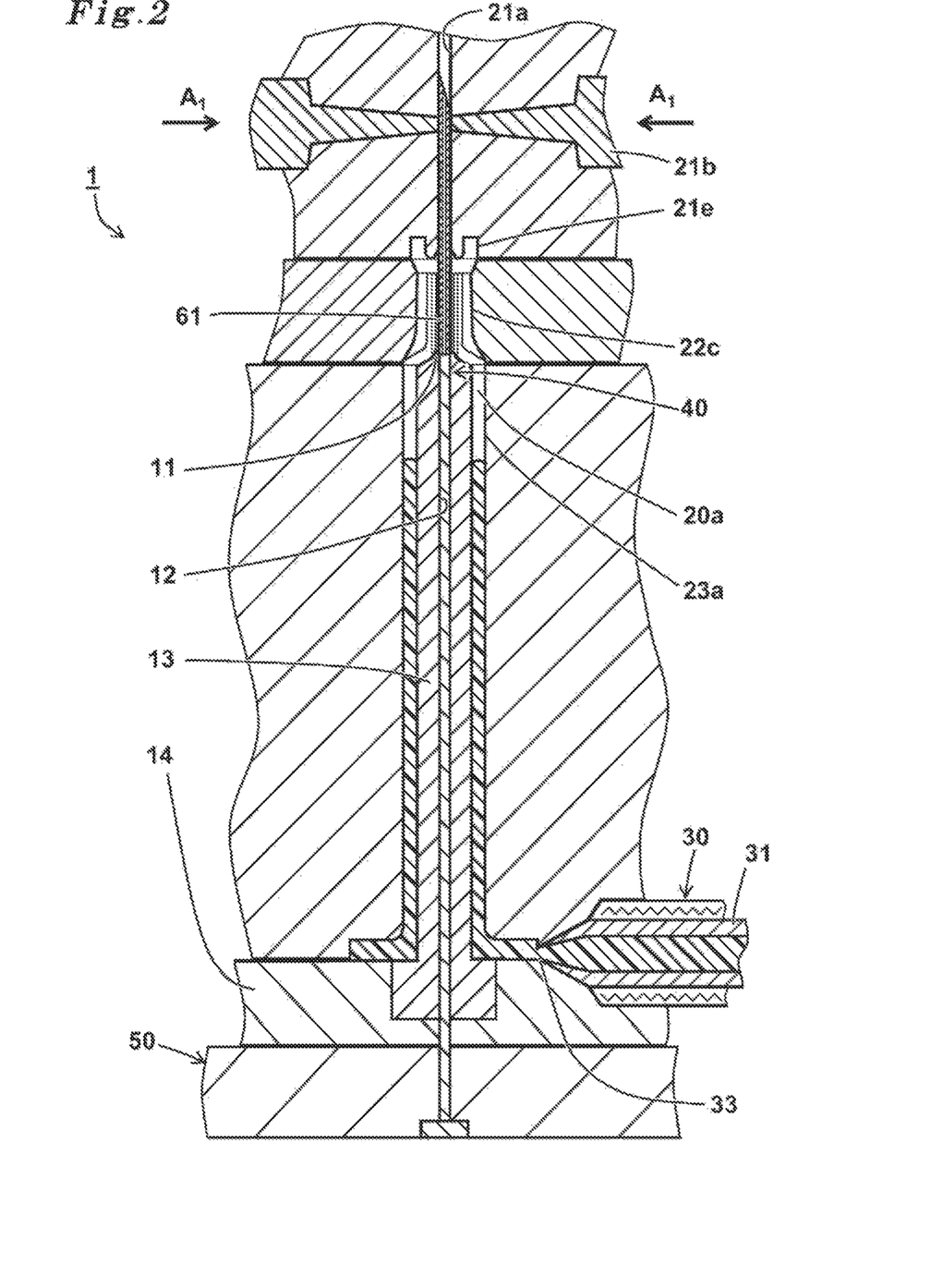
FIG. 2 is a schematic cross-sectional front view of a state in which the injection needle is pushed up and resin is injected while the injection molding die of one embodiment is used.
Figure 3:
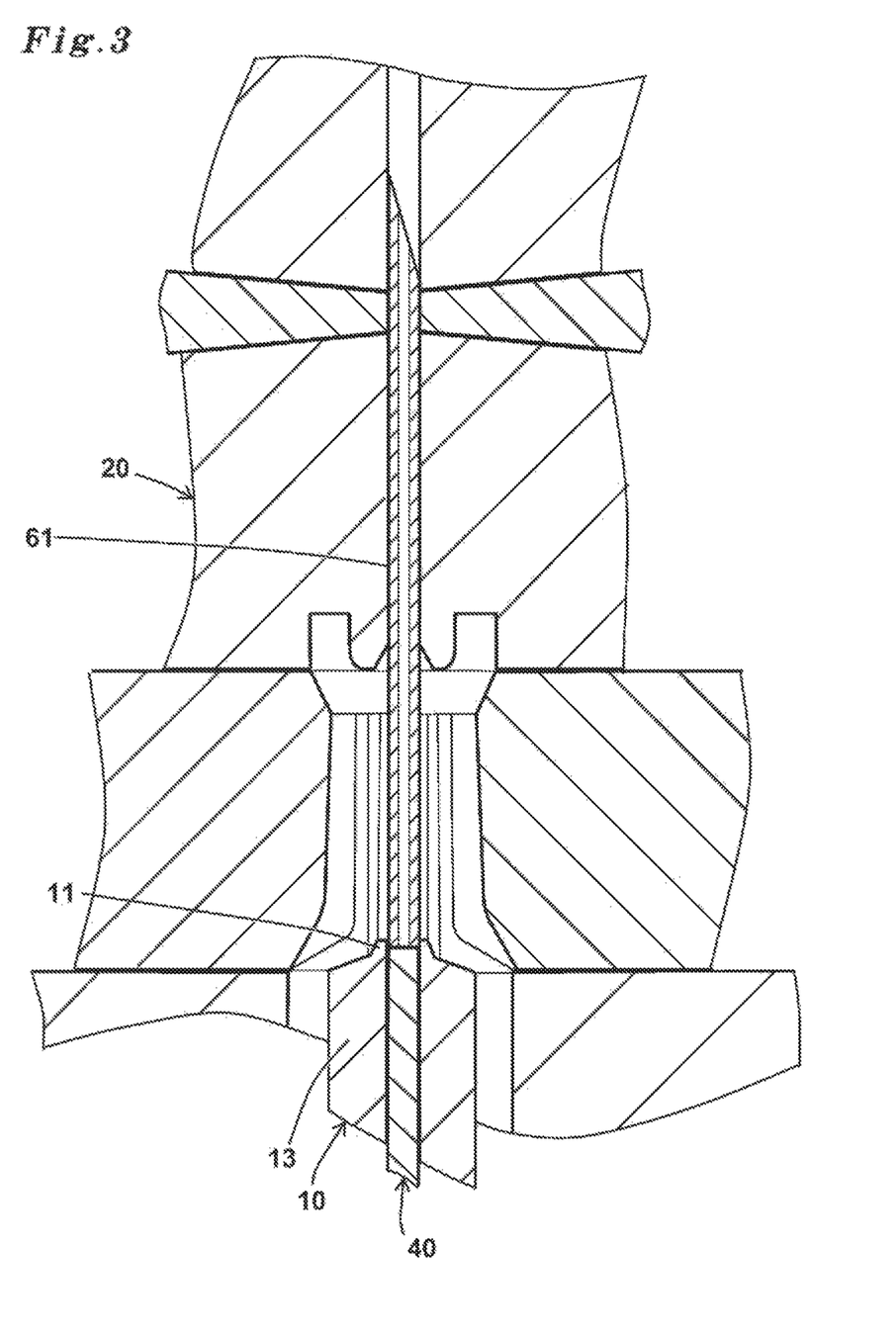
FIG. 3 is an enlarged partial cross-sectional front view of the main parts of the injection molding die according to one embodiment of the present invention.

Next, as illustrated in FIGS. 1 and 2, while the injection needle holding hole 21a, the nozzle forming space 22c, the body forming space 23a, the head forming space 21e, and the core pin 13 are coaxially held, the drive plate 50 moves in a closing direction $A_5$ until the drive plate 50 comes into contact with the fixing plate 14. In response to the movement, the support rod 40 connected to the drive plate 50 lunges upward and pushes up the needle proximal end of the injection needle 61 to the vicinity of the distal end of the protrusion 11. The needle proximal end of the injection needle 61 moves to a position higher than the clamping units 21b. Meanwhile, the proximal end of the injection needle 61 is pushed up immediately under the distal end of the protrusion 11 highly enough to prevent the resin from flowing from the needle proximal end into the hole of the injection needle 61. The injection needle 61 is pushed up in the injection needle holding hole 21a and held in a state in which the central axis of the injection needle 61 is aligned with the central axis of the core pin 13. This can minimize the size of the protrusion 11 in the injection molding die 1 (see FIG. 3), and thus can extremely reduce the size of the recessed part 64 formed by the transfer of the protrusion 11 on the inner wall of the barrel 62 of the needle-equipped syringe 60. Thus, the recessed part 64 can be a dead space.

However, the size of the recessed part 64 can be reduced approximately to a few percentages or a few tenths of that of a needle-equipped syringe that is molded with deeply insertion of the injection needle 61 into the core pin 13 to minimize inclination of the injection needle 61 as in the prior art (see FIG. 6).

After that, the clamping units 21b move in a closing direction $A_1$. This movement can fix the injection needle 61 in a state in which the injection needle 61 is substantially arranged coaxially with the core pin 13. After the injection molding die 1 is clamped, the melt resin is injected through the runner 31 from the resin injection gate 33 to the cavity 20a for injection molding to mold the needle-equipped syringe 60.

During the injection molding, the cavity 20a corresponding to the flange 68, body 65, nozzle part 63 of the needle-equipped syringe 60 is filled with the thermally-melt thermoplastic resin sequentially. The resin is continuously filled for a while, and the cavity 20a is completely filled with the resin to a position corresponding to the head 63a of the nozzle part 63. The thermally-melt resin in the cavity 20a is cooled and solidified. Meanwhile, the injection needle 61 is held at a predetermined position and the needle proximal end is slightly embedded in the protrusion 11. This prevents the resin from entering the needle hole from the proximal end, and solidifies the resin so that the resin surrounds substantially half of the injection needle 61 in the nozzle forming space 22c. As a result, the injection needle 61 is firmly fixed to and held on the barrel 62 without blocking the needle hole. Meanwhile, the core pin 13 placed in the cavity 20a forms an internal hollow 66 of the barrel 62 to be filled with drug solution and an opening part 67 from which the drug solution is injected in the internal hollow 66. The concave part 24 of the cavity 20a forms the outer wall of the barrel 62 (see FIG. 4A).

After that, when the resin is solidified, the clamping units 21b are moved and opened in a direction opposite to the closing direction $A_1$ so that the needle holding female die 21 is movable. Subsequently, the needle holding female die 21 is moved in a direction opposite to the closing direction $A_2$. Furthermore, the nozzle part forming female die 22 is divided into the left die $22_L$ and the right die $22_R$, and moved in a direction opposite to the closing direction $A_3$. After that, the body forming female die 23 is moved in a direction opposite to the closing direction $A_4$ so that the injection molding die 1 is opened. The molded needle-equipped syringe 60 is removed from the core pin 13. The burr formed on the flange 68 due to the resin injection gate 33 is removed as necessary.

The needle-equipped syringe 60 of the embodiment produced as described above is formed of the barrel 62 made of resin and the injection needle 61 integrated with the nozzle part 63 of the barrel 62 as illustrated in FIG. 4A.

The barrel 62 is formed in a cylindrical shape and includes: the body 65 including the internal hollow 66 to be filled with drug solution, and formed of the nozzle part 63 provided on the distal end of the barrel 62 and the peripheral wall continuously formed around the nozzle part 63 and extending toward the proximal end; and the opening part 67 provided on the proximal end. The opening part 67 includes the flange 68 extending outward and vertically to the axis of the body 65. The flange 68 includes only a gate mark 69 on the external surface of the flange 68. The gate mark is left with the resin injection gate 33 when the needle-equipped syringe 60 is formed.

The injection needle 61 penetrates the nozzle part 63. The nozzle part 63 includes the recessed part 64 that is formed by the transfer of protrusion 11 and is formed substantially in a frustum of a cone on the internal surface of the nozzle part 63.

The outer diameter of the recessed part 64 is equal to or smaller than 1.5 mm, and is preferably equal to or smaller than 1.0 mm, and more preferably equal to or smaller than 0.5 mm. The depth of the recessed part 64 is equal to or lower than 1.5 mm, and is preferably equal to or lower than 1.0 mm, and more preferably equal to or lower than 0.5 mm. Note that the smaller recessed part 64 is more preferable. The recessed part 64 is not necessarily required.

The needle proximal end of the injection needle 61 slightly protrudes from the recessed part 64 to the internal hollow 66 of the body 65. The length of the needle proximal end protruding to the internal hollow 66 is equal to or shorter than 1.5 mm, and is preferably equal to or shorter than 1.0 mm, and more preferably equal to or shorter than 0.5 mm, and more preferably 0 mm. This can minimize the dead space formed between the proximal end of the injection needle 61 and the distal end (bottom) of the recessed part 64 corresponding to the distal end of the protrusion 11 in the recessed part 64. Even when the dead space is filled with the drug solution, the amount of the filled drug solution is extremely small. Thus, the filled drug solution is completely discharged. The complete discharge contributes to the efficient usage of the drug solution.

The injection needle 61 is held in a state in which the part from the center to the tip of the distal end of the injection needle 61 protrudes from the nozzle part 63 toward a side on the distal end of the nozzle part 63.

The axis of the held injection needle 61 is not inclined at all or is hardly inclined. This preferably makes the held injection needle 61 substantially parallel to the axis of the outer peripheral surface of the body 65. The substantial parallelism means that the axis of the injection needle 61 is absolutely parallel to the axis of the outer peripheral surface of the body 65 of the barrel 62, or that the central axis of the injection needle 61 is inclined at an angle of two degrees or less with respect to the central axis of the outer peripheral surface of the body 65.

The nozzle part 63 includes the pleated skirt 63c and the head 63a. The circular head 63a of which diameter is expanded to some degree is mounted on the pleated skirt 63c, and includes a circular incline 63b that is the center of the circular recessed part of the head 63a bulging in a conical shape and penetrated by the injection needle 61.

The recessed part 64 can substantially be formed in a frustum of a cone, a hemispherical shape, or a frustum of a pyramid, depending on the shape of the protrusion 11.

The center of the head 63a can bulge in a domical shape around the injection needle 61, depending on the shape of the inclined part 21d.

The pleated skirt 63c of the nozzle part 63 can have a polygonal prism shape such as quadrangular prisms or hexagonal prisms or a columnar shape that enables the nozzle part 63 to maintain the strength to hold the injection needle 61.

The resin to form the barrel 62 is selected in terms, for example, of the chemical resistance, heat resistance, gas and/or bacteria barrier property, safety of a living body, and transparency. Thermoplastic resin, for example, polyolefin resin such as polyethylene, polypropylene, and cyclo-olefin polymers; polystyrene; polycarbonate; or polyester such as polyethylene terephthalate; polyamide is used. Especially, cyclic olefin homopolymer or cyclic olefin copolymer is preferably used because such resins are transparent enough to visually confirm the contained drug solution from the outside and have a little interaction with the drug solution.

The injection needle 61 is made of a material durable enough to be used for injection molding, and selected in terms, for example, of the chemical resistance, heat resistance, gas and/or bacteria barrier property, and safety of a living body. For example, stainless steel and nickel-free stainless steel can be cited as the material. Stainless steel relatively easy to form and inexpensive is preferable.

The position where the nozzle part 63 holds the needle proximal end of the injection needle 61 is not necessarily the center of the nozzle part 63. The position can be moved from the center in a radial direction of the body 65 to some degree. Alternatively, the injection needle 61 can be inserted into the through hole 12 after the bevel of the injection needle 61 is detected with a sensor and the orientation of the injection needle 61 is adjusted so that the bevel faces the flange 68.

Figure 5:
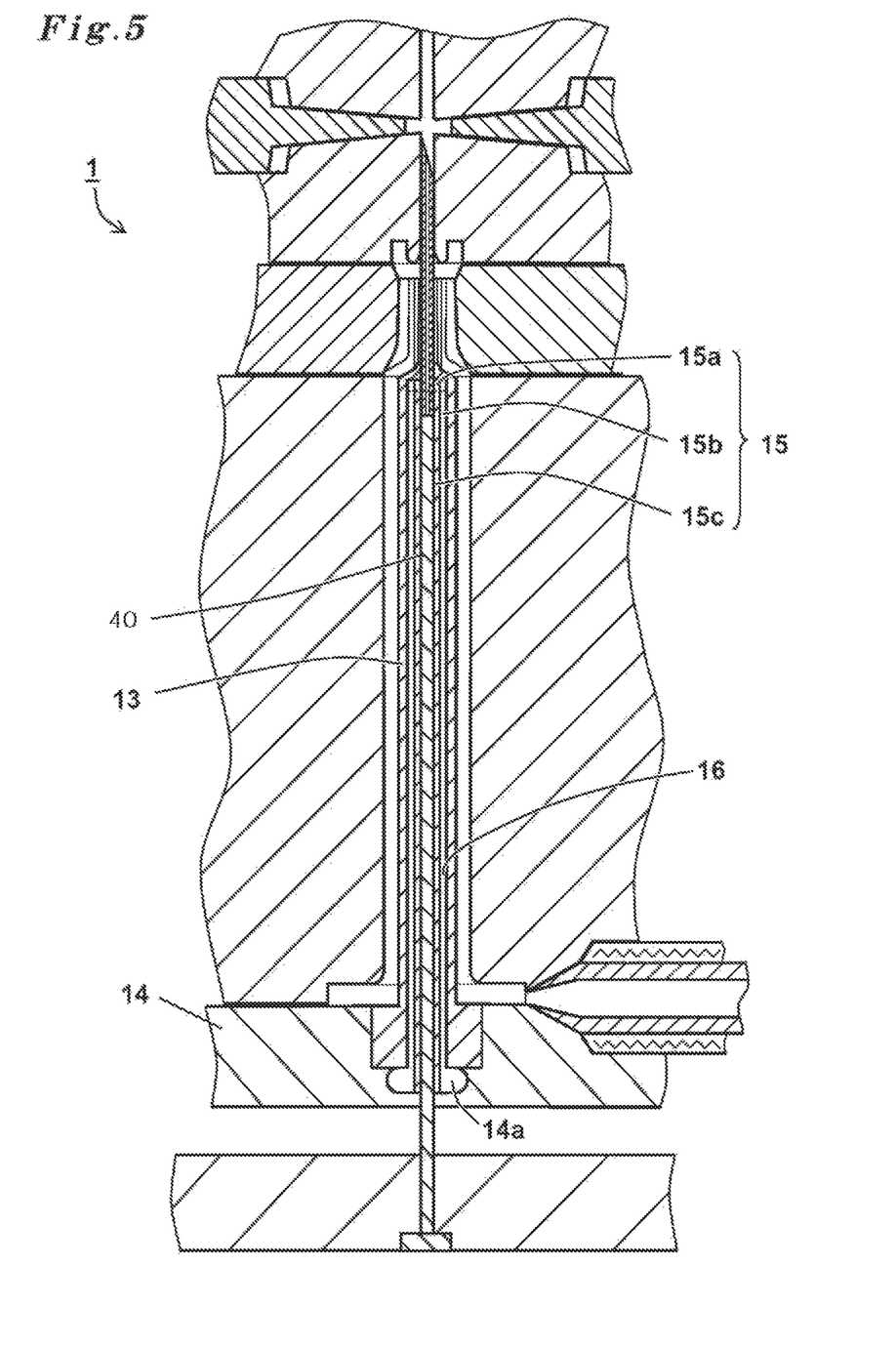
FIG. 5 is a schematic cross-sectional front view of another embodiment of the injection molding die of the present invention.

FIG. 5 is a schematic cross-sectional front view of another embodiment of the injection molding die 1. The injection molding die 1 includes a core pin 13 including a cooling mechanism in the core pin 13 instead of the core pin 13 illustrated in FIG. 1. The cooling mechanism cools the thermally-melt thermoplastic resin injected from the resin injection gate 33 by heat conduction, and is, for example, a water cooling mechanism in which cooling water flows for heat exchange.

Specifically, the cooling mechanism includes a groove through which cooling water flows in the core pin 13. The inside of the core pin 13 is cylindrically hollowed and a cylindrical core 15 is fitted and screwed to the hollowed inside. The core pin 13 is provided with the through hole 12 penetrating the central axis of the core pin 13 including the core 15 from the needle distal end to needle proximal end of the core pin 13.

The core 15 is provided with a pair of longitudinal grooves 15b on the side surfaces of the core rod 15c symmetrically with respect to the core rod 15c from the lower end to upper end of the core rod 15c. The core 15 is provided with a lateral groove 15a formed in a semi-circle and connecting the upper ends of the longitudinal grooves 15b. The lower ends of the longitudinal grooves 15b are connected to a pipe 14a provided in the fixing plate 14 so that the cooling water flows from one longitudinal groove 15b through the lateral groove 15a to another longitudinal groove 15b. The cooling water flowing in the lateral groove 15a and the longitudinal grooves 15b flows in the flow path in the core pin 13 so as to cool and solidify the thermally-melt resin injected in the cavity 20a in the injection molding die 1.

Note that the cooling mechanism can be a thermal conductive metal rod cooled by a cooling medium.

INDUSTRIAL APPLICABILITY

A method for producing a needle-equipped syringe using the injection molding die of certain embodiments of the present invention can be used to produce a needle-equipped syringe in which there is a small dead space and the injection needle is not inclined with respect to the barrel. The needle-equipped syringe can be used for hypodermic injection, for example, of a biological product such as a vaccine.

REFERENCE SIGNS LIST

1 Injection molding die
10 Male die
11 Protrusion

12 Through hole
13 Core pin
14 Fixing plate
14a Pipe
15 Core
15a Lateral groove
15b Longitudinal groove
15c Core rod
16 Insertion unit
20 Female die
20a Cavity
21 Needle holding female die
21a Injection needle holding hole
21b Clamping unit
21c Convex part
21d Inclined part
21e Head forming space
22 Nozzle part forming female die
$22_L$ Left die
$22_R$ Right die
22c Nozzle forming space
23 Body forming female die
23a Body forming space
23b Female die opening part
24 Concave part
30 Resin injection nozzle
31 Runner
32 Heater
33 Resin injection gate
40 Support rod
50 Drive plate
60 Needle-equipped syringe
61 Injection needle
62 Barrel
63 Nozzle part
63a Head
63b Circular incline
63c Pleated skirt
64 Recessed part
65 Body
66 Internal hollow
67 Opening part
68 Flange
69 Gate mark
$A_1, A_2, A_3, A_4, A_5$ Closing direction

What is claimed is:

1. A method for producing a needle-equipped syringe using an injection molding die, the needle-equipped syringe including a barrel and an injection needle, the barrel including a cylindrical body, a nozzle part located on a distal end of the cylindrical body, and an opening part provided on a proximal end of the cylindrical body, the barrel being made of resin, the injection needle including a needle distal end and a needle proximal end, the needle proximal end being held by the nozzle part, the method comprising:
   providing a male die including:
      a core pin, and
      a through hole,
      wherein the core pin includes a core pin distal end and a core pin proximal end, and is configured to form an internal surface of the barrel,
      wherein the through hole extends through the core pin from the core pin distal end to the core pin proximal end,
   providing a female die including:
      a female die opening part,
      a concave part, and
      an injection needle holding hole,
      wherein the concave part communicates with the female die opening part, and is configured to form an external surface of the barrel,
      wherein the injection needle holding hole is located on a side opposite to the female die opening part and coaxially with the through hole of the male die,
      wherein the injection needle holding hole communicates with the concave part,
   providing a support rod that is inserted from the core pin proximal end into the through hole;
   inserting the injection needle from the needle proximal end into the through hole from the core pin distal end, and contacting and supporting the needle proximal end of the injection needle with the support rod;
   forming a cavity defined by the concave part and the core pin by inserting the core pin, with the injection needle inserted in the through hole, from the female die opening part into an internal hollow of the concave part;
   pushing the needle proximal end to a vicinity of the core pin distal end by pushing the support rod inserted in the through hole, such that a portion of the injection needle is in the cavity, and a portion of the injection needle is held in the injection needle holding hole; and
   forming the needle-equipped syringe in which the needle proximal end of the injection needle is held by the nozzle part of the barrel by injecting the resin into the cavity.

2. The method for producing a needle-equipped syringe according to claim 1, the support rod is pushed until a distance between a distal end of the support rod and the core pin distal end is 1.5 mm or less.

3. The method for producing a needle-equipped syringe according to claim 1, wherein the core pin includes a protrusion on the core pin distal end, the protrusion being configured to prevent the resin from entering the injection needle by surrounding the needle proximal end, and
   a recessed part corresponding to the protrusion is formed in the barrel when the resin is injected into the cavity, and the needle proximal end is embedded in the recessed part.

4. The method for producing a needle-equipped syringe according to claim 1, wherein an outer diameter of the protrusion is 1.5 mm or less, and a height of the protrusion is 1.5 mm or less.

5. The method for producing a needle-equipped syringe according to claim 1,
   wherein clamping units configured to clamp the injection needle in the injection needle holding hole are located in the female die, and
   wherein after pushing the injection needle with the support rod, the injection needle, while supported by the support rod in the injection needle holding hole, is clamped by the clamping units.

6. The method for producing a needle-equipped syringe according to claim 1,
   wherein a cooling mechanism configured to cool the resin injected from the resin injection gate by thermal conduction is located in the core pin, and
   the method further comprises cooling and solidifying the resin injected in the cavity with the cooling mechanism, and removing the injection needle and barrel.

* * * * *